(12) United States Patent
Alromaih et al.

(10) Patent No.: US 10,835,273 B1
(45) Date of Patent: Nov. 17, 2020

(54) SURGICAL INSTRUMENT FOR THE REMOVAL OF FRONTAL NASAL RECESS CELLS

(71) Applicant: KING SAUD UNIVERSITY, Riyadh (SA)

(72) Inventors: Saud Romaih Alromaih, Riyadh (SA); Ibrahim Ali Sumaily, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 16/805,799

(22) Filed: Mar. 1, 2020

(51) Int. Cl.
*A61B 17/24* (2006.01)

(52) U.S. Cl.
CPC ........ *A61B 17/24* (2013.01); *A61B 2017/246* (2013.01)

(58) Field of Classification Search
CPC .......... A61M 25/0017; A61M 25/0043; A61M 25/0067; A61M 25/0068; A61M 27/00; A61M 29/00; A61M 31/00; A61M 2210/00618; A61M 2210/0681; A61B 17/22; A61B 17/24; A61B 2017/246; A61B 2090/0817; A61B 1/233
See application file for complete search history.

(56) References Cited

U.S. PATENT DOCUMENTS

| | | | |
|---|---|---|---|
| 5,546,739 A | 8/1996 | Hettich | |
| 6,312,438 B1 | 11/2001 | Adams | |
| D634,838 S | 3/2011 | Dolezal | |
| 8,858,974 B2 | 10/2014 | Eaton et al. | |
| 10,065,028 B2 | 9/2018 | Liberatore et al. | |
| 2005/0100860 A1* | 5/2005 | Kameli ................ | A61C 3/08 433/144 |
| 2010/0063532 A1 | 3/2010 | Moore | |
| 2016/0128709 A1 | 5/2016 | Covello | |
| 2017/0080179 A1 | 3/2017 | Rotenberg | |

FOREIGN PATENT DOCUMENTS

| | | |
|---|---|---|
| CN | 2912536 Y | 6/2007 |
| CN | 209136720 U | 7/2019 |

OTHER PUBLICATIONS

Item 44-955, "Kuhn frontal sinus seeker, double-ended, size #2," ® 2020 Ambler Surgical website: https://amblersurgical.com/44-955-kuhn-frontal-sinus-seeker-double-ended-size-2.

* cited by examiner

*Primary Examiner* — Robert A Lynch
(74) *Attorney, Agent, or Firm* — Nath, Goldberg & Meyer; Richard C. Litman

(57) ABSTRACT

A surgical instrument for the removal of frontal nasal recess cells includes an elongate handle, a first arm extending from a first end of the handle and a second arm extending from a second end of the handle. The first and second arms can extend in opposing directions. Each of the arms include a spherical terminal hub on their respective ends. A plurality of cylindrical fingers extend from each terminal hub at an angle, thereby providing an umbrella-like configuration. A spherical cap is attached to a free end of each cylindrical finger.

11 Claims, 3 Drawing Sheets

SURGICAL INSTRUMENT FOR THE REMOVAL OF FRONTAL NASAL RECESS CELLS

BACKGROUND

1. Field

The disclosure of the present patent application relates to surgical instruments, and particularly, to a surgical instrument for the removal of frontal nasal recess cells.

2. Description of the Related Art

Chronic sinusitis is a very common medical problem. It can be managed both medically and surgically. The surgical treatment of chronic sinusitis involves functional endoscopic sinus surgery. This surgery is conducted hundreds of thousands of times annually in the United States. The surgery is intended to open all diseased sinuses to thereby restore the natural flow of their mucous secretions. An integral part of the success of this surgery is to avoid missing a diseased sinus. The frontal sinus is the most anterior and superior sinus relative to the nostrils. This anatomical relation of the frontal sinus to the nostrils makes it the most difficult sinus tissue to treat. In addition, the wide variety in the individual anatomy of the frontal recess results in different types of air-cells surrounding the frontal drainage pathway.

Rhinologists typically remove air-cells using a surgical seeker to locate the frontal sinus drainage pathway. Conventional methods for performing this procedure are lengthy and can require the use of multiple instruments.

Thus, a surgical instrument for the removal of frontal nasal recess cells solving the aforementioned problems is desired.

SUMMARY

A surgical instrument for the removal of frontal nasal recess cells includes an elongate handle, a first arm extending from a first end of the handle and a second arm extending from a second end of the handle. The first and second arms can extend in opposing directions. Each of the arms include a spherical terminal hub on their respective free ends. A plurality of cylindrical fingers extend from each terminal hub at an angle, thereby providing an umbrella-like configuration. In an embodiment, five cylindrical fingers extend from each terminal hub. A spherical cap is attached to a free end of each cylindrical finger.

The surgical instrument for the removal of frontal nasal recess cells can remove the frontal recess air-cells surrounding the frontal drainage pathway with only a few strokes of the instrument, thereby helping surgeons achieve good frontal sinus drainage in less time. In addition, the different sized arms of the instrument reduce the need for using other frontal sinus instruments.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
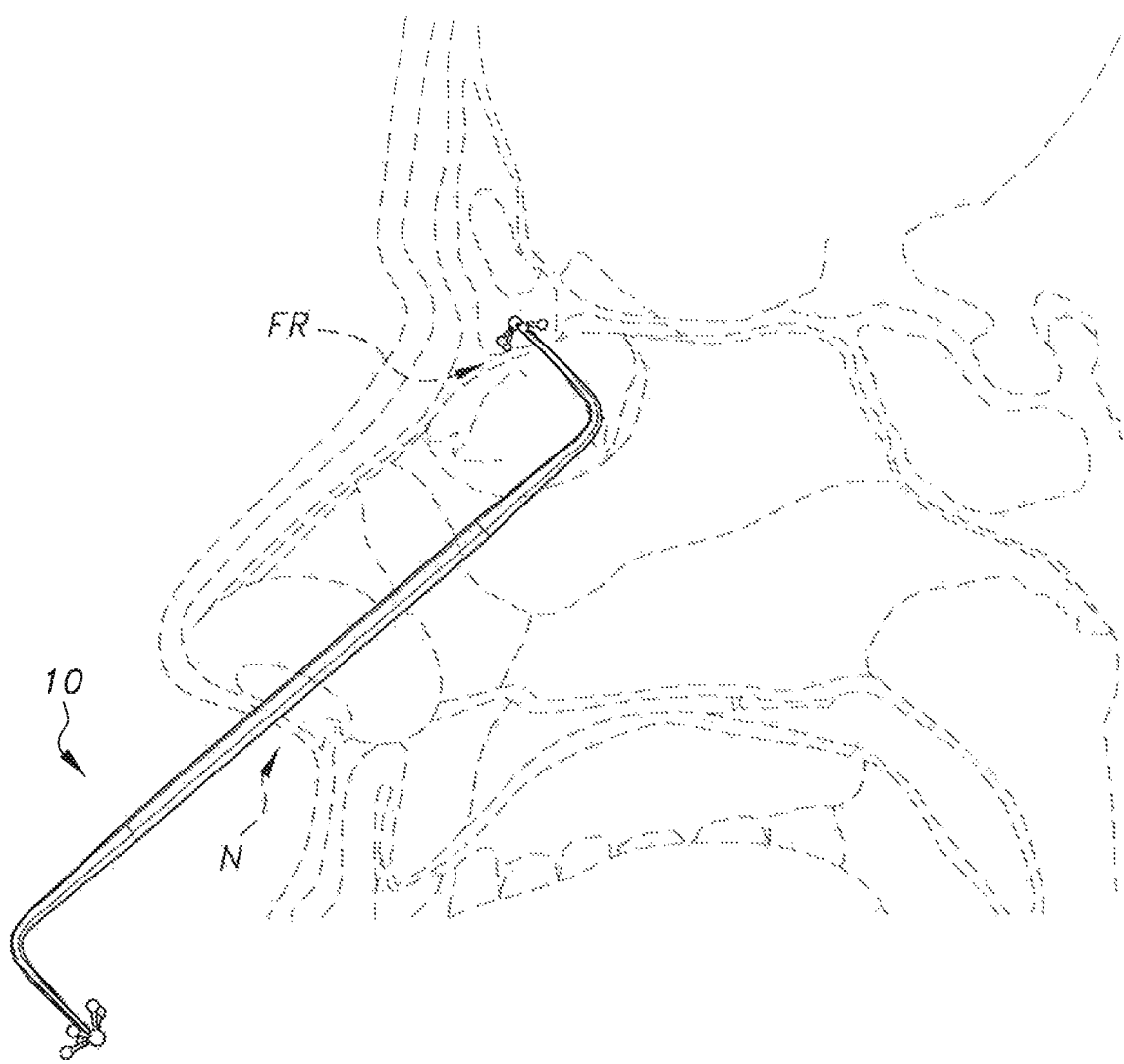
FIG. 1 is a perspective, environmental view of a surgical instrument for the removal of frontal nasal recess cells being used to remove frontal nasal recess cells.
Figure 2:
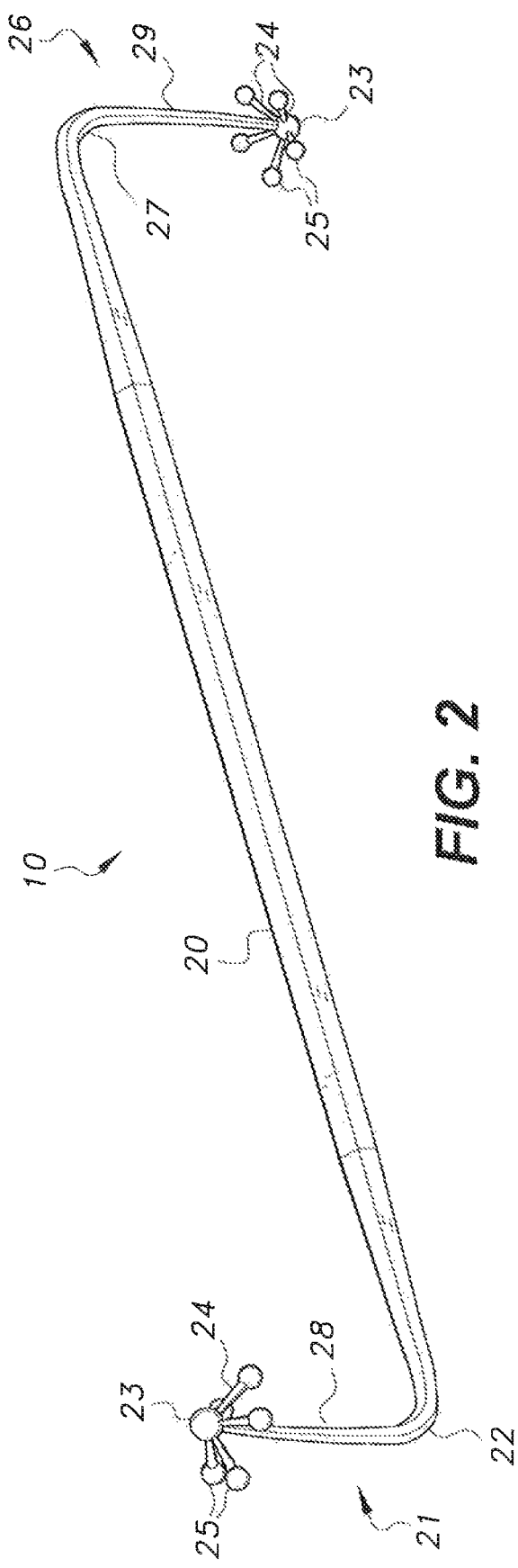
FIG. 2 is perspective view of the surgical instrument for the removal of frontal nasal recess cells of FIG. 1.

The surgical instrument for the removal of frontal nasal recess cells 10 is shown in FIG. 1 with one end inserted into the patient's frontal recess FR through a patient's nostril N to remove frontal nasal recess cells. The details of the instrument are shown in FIGS. 2-4.

As used herein, the term "about," when used to modify a numerical value, means within ten percent of that numerical value.

The instrument 10 includes an elongate handle 20, a first arm 28 extending from a first end 21 of the handle 20 and a second arm 29 extending from a second end 26 of the handle 20. The first and second arms 28, 29 can extend in opposing directions. In an embodiment, the first arm 28 and the handle 20 can intersect at a first corner 22, forming an angle of about 90 degrees. In an embodiment, the second arm 29 and the handle 20 can intersect at a second corner 27, forming an angle of about 90 degrees. Each of the arms 28, 29 include a spherical terminal hub 23 on their respective ends. A plurality of cylindrical fingers 24 extend from each terminal hub 23 at an angle, thereby providing an umbrella-like configuration. In an embodiment, five cylindrical fingers extend from each terminal hub 23. A spherical cap 25 is attached to a free end of each cylindrical finger 24.

Figure 3:
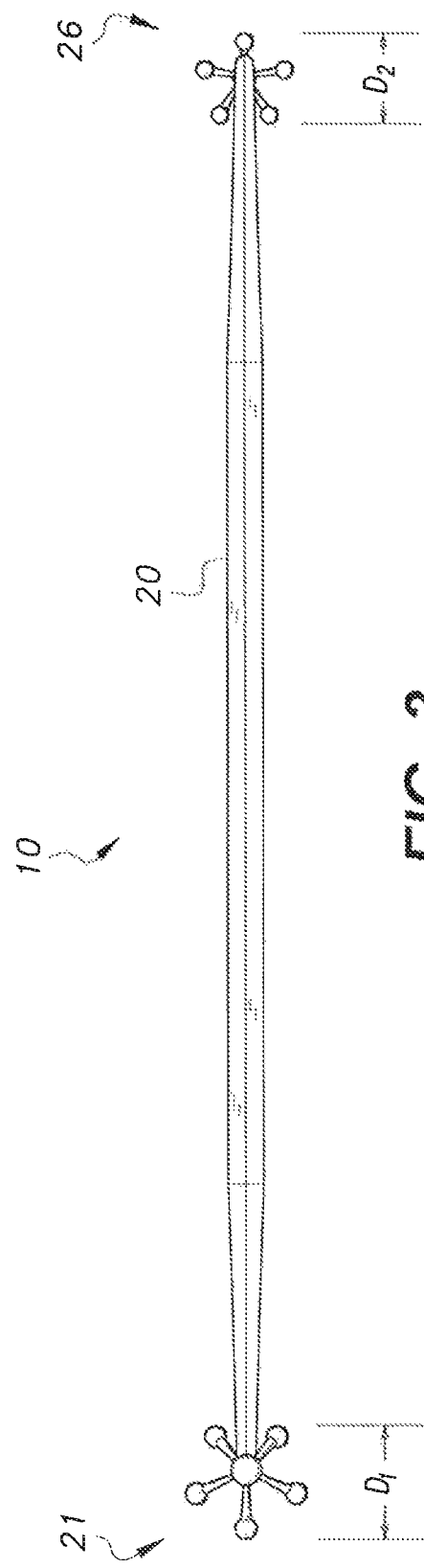
FIG. 3 is top view of the surgical instrument for the removal of frontal nasal recess cells of FIG. 1.
Figure 4:
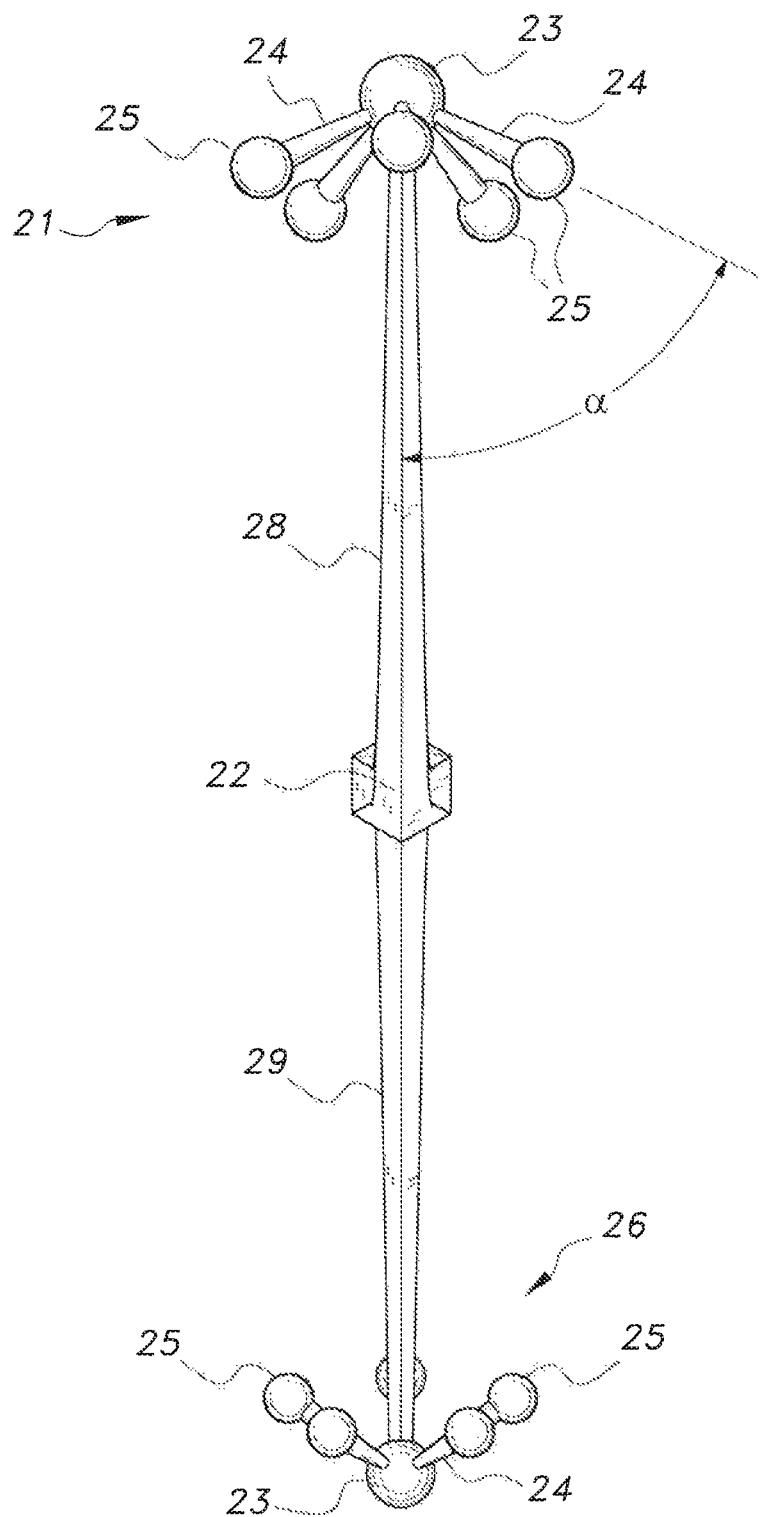
FIG. 4 is a left end view of the surgical instrument for the removal of frontal nasal recess cells of FIG. 1.

As best seen in FIG. 3, a distance D1 between non-adjacent spherical caps 25 of the first arm 28 can be greater than a distance D2 between non-adjacent spherical caps 25 of the second arm 29. In some embodiments, D1 equals 5 mm and a length of the fingers extending from the terminal hub of the first arm is 2.5 mm. In an embodiment, D2 equals 3 mm and a length of the fingers extending from the terminal hub of the second arm is 1.5 mm. In some embodiments, the length of the handle 20 from the first corner 22 to the second corner 27 is 15 cm.

As is best seen in FIG. 4, the cylindrical fingers 24 extend outwardly from the terminal hubs 23 at an angle α from the arms 28, 29, to form the skeletal umbrella-like configuration. In some embodiments, the angle α can be less than 90°.

The surgical instrument for the removal of frontal nasal recess cells 10 can be formed in any suitable manner, e.g., 3D printing and may be made of any suitable material.

It is to be understood that the surgical instrument for the removal of frontal nasal recess cells is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A surgical instrument for the removal of frontal nasal recess cells, comprising:
    an elongate handle;

a first arm extending from a first end of the handle, wherein the first arm extends substantially perpendicular to the handle;

a second arm extending from a second end of the handle, wherein the second arm extends substantially perpendicular to the handle;

a spherical terminal hub extending from a tip of each of the first arm and the second arm;

a plurality of cylindrical fingers extending from each terminal hub at an angle; and a spherical cap positioned at a free end of each cylindrical finger.

2. The surgical instrument for the removal of frontal nasal recess cells as recited in claim 1, wherein the first arm and the second arm extend in opposing directions.

3. The surgical instrument for the removal of frontal nasal recess cells as recited in claim 1, wherein five cylindrical fingers extend from each terminal hub.

4. The surgical instrument for the removal of frontal nasal recess cells as recited in claim 3, wherein a distance between non-adjacent spherical caps of the first arm is about 5 mm and a distance between non-adjacent spherical caps of the second arm is about 3 mm.

5. The surgical instrument for the removal of frontal nasal recess cells as recited in claim 4, wherein a length of the fingers extending from the terminal hub of the first arm is about 2.5 mm and a length of the fingers extending from the terminal hub of the second arm is about 1.5 mm.

6. The surgical instrument for the removal of frontal nasal recess cells as recited in claim 1, wherein the length of the handle is about 15 cm.

7. A surgical instrument for the removal of frontal nasal recess cells, comprising:

an elongate handle;

a first arm extending substantially perpendicular to a first end of the handle;

a second arm extending substantially perpendicular to a second end of the handle, the second arm extending in a direction opposite the first arm;

a spherical terminal hub extending from a tip of each of the first arm and the second arm;

a plurality of cylindrical fingers extending from each terminal hub at an angle; and a spherical cap positioned at a free end of each cylindrical finger.

8. The surgical instrument for the removal of frontal nasal recess cells as recited in claim 7, wherein five cylindrical fingers extend from each terminal hub.

9. The surgical instrument for the removal of frontal nasal recess cells as recited in claim 7, wherein a distance between non-adjacent spherical caps of the first arm is about 5 mm and a distance between non-adjacent spherical caps of the second arm is about 3 mm.

10. The surgical instrument for the removal of frontal nasal recess cells as recited in claim 9, wherein a length of the fingers extending from the terminal hub of the first arm is about 2.5 mm and a length of the fingers extending from the terminal hub of the second arm is about 1.5 mm.

11. The surgical instrument for the removal of frontal nasal recess cells as recited in claim 10, wherein the length of the handle is about 15 cm.

* * * * *